(12) United States Patent
Ammermann et al.

(10) Patent No.: US 8,188,001 B2
(45) Date of Patent: *May 29, 2012

(54) FUNGICIDAL MIXTURES

(75) Inventors: Eberhard Ammermann, Heppenheim (DE); Reinhard Stierl, Mutterstadt (DE); Gisela Lorenz, Neustadt (DE); Ulrich Schöfl, Brühl (DE); Siegfried Strathmann, Limburgerhof (DE); Klaus Schelberger, Gönnheim (DE); Thomas Christen, Dannstadt-Schauernheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 100 days.

This patent is subject to a terminal disclaimer.

(21) Appl. No.: 12/640,423

(22) Filed: Dec. 17, 2009

(65) Prior Publication Data

US 2010/0160399 A1    Jun. 24, 2010

Related U.S. Application Data

(63) Continuation of application No. 10/508,208, filed as application No. PCT/EP2003/002845 on Mar. 19, 2003, now Pat. No. 7,683,086.

(30) Foreign Application Priority Data

Mar. 21, 2002   (DE) ................. 102 12 704

(51) Int. Cl.
*A01N 25/26* (2006.01)
*A01N 43/00* (2006.01)
*A01N 43/64* (2006.01)
*A01N 25/00* (2006.01)

(52) U.S. Cl. ......... 504/100; 504/139; 514/384; 424/405
(58) Field of Classification Search .......... None
See application file for complete search history.

(56) References Cited

U.S. PATENT DOCUMENTS

| | | | |
|---|---|---|---|
| 3,017,415 A | 1/1962 | Sarett et al. | |
| 3,249,499 A | 5/1966 | von Schmeling et al. | |
| 3,657,443 A | 4/1972 | Klopping et al. | |
| 3,905,798 A | 9/1975 | Zeeh et al. | |
| 3,991,071 A | 11/1976 | Brookes et al. | |
| 4,001,297 A | 1/1977 | Noguchi et al. | |
| 4,151,299 A | 4/1979 | Hubele | |
| 4,321,174 A | 3/1982 | Hoy et al. | |
| 4,705,800 A | 11/1987 | Nyfeler et al. | |
| 4,780,551 A | 10/1988 | Nyfeler et al. | |
| 4,849,219 A * | 7/1989 | Staub et al. ............ | 424/605 |
| 4,925,840 A | 5/1990 | Nyfeler et al. | |
| 5,330,995 A | 7/1994 | Eicken et al. | |
| 5,480,897 A | 1/1996 | Eicken et al. | |
| 5,556,988 A | 9/1996 | Eicken et al. | |
| 5,589,493 A | 12/1996 | Eicken et al. | |
| 5,679,866 A | 10/1997 | Curtze et al. | |
| 5,773,663 A | 6/1998 | Curtze et al. | |
| 5,789,430 A | 8/1998 | Jautelat et al. | |
| 5,847,005 A | 12/1998 | Kasahara et al. | |
| 5,859,039 A | 1/1999 | Jautelat et al. | |
| 5,866,722 A | 2/1999 | Curtze et al. | |
| 5,922,905 A | 7/1999 | Curtze et al. | |
| 5,922,919 A | 7/1999 | Curtze et al. | |
| 5,942,538 A | 8/1999 | Kasahara et al. | |
| 5,945,567 A | 8/1999 | Curtze et al. | |
| 6,001,883 A | 12/1999 | Curtze et al. | |
| 6,306,850 B1 | 10/2001 | Dutzmann et al. | |
| 6,346,535 B1 | 2/2002 | Cotter et al. | |
| 6,417,398 B1 | 7/2002 | Eicken et al. | |
| 6,420,605 B1 | 7/2002 | Eicken et al. | |
| 6,436,979 B1 | 8/2002 | Schelberger et al. | |
| 6,509,501 B2 | 1/2003 | Eicken et al. | |
| 7,683,086 B2 * | 3/2010 | Ammermann et al. ....... | 514/384 |
| 2002/0072535 A1 | 6/2002 | Stenzel et al. | |
| 2002/0173529 A1 | 11/2002 | Dutzmann et al. | |
| 2003/0078437 A1 | 4/2003 | Eicken et al. | |
| 2003/0120085 A1 | 6/2003 | Eicken et al. | |
| 2003/0158151 A1 | 8/2003 | Wachendorff-Neumann et al. | |
| 2004/0127739 A1 | 7/2004 | Kunz et al. | |
| 2004/0209923 A1 | 10/2004 | Berger et al. | |

FOREIGN PATENT DOCUMENTS

| | | |
|---|---|---|
| CA | 1314809 | 3/1993 |
| EP | 0236689 A2 | 9/1987 |
| EP | 0539332 A1 | 4/1993 |
| EP | 0677246 A1 | 10/1995 |
| EP | 0714605 A1 | 6/1996 |
| EP | 899255 A2 | 8/1997 |
| EP | 967196 A2 | 6/1998 |
| EP | 1 023 834 A1 | 8/2000 |
| EP | 1077028 A1 | 2/2001 |
| GB | 2262037 * | 6/1993 |
| GB | 2262037 A | 6/1993 |
| GB | 2299509 A | 10/1996 |
| GB | 857383 | 12/2009 |
| WO | 0249434 A1 | 6/2002 |
| WO | 02054870 A2 | 7/2002 |

OTHER PUBLICATIONS

The Pesticide Manual (12):39-40, 2000.

* cited by examiner

*Primary Examiner* — Alton Pryor
(74) *Attorney, Agent, or Firm* — Rothwell, Figg, Ernst & Manbeck, P.C.

(57) ABSTRACT

The invention relates to a fungicidal mixture comprising prothioconazole or a salt or adduct thereof with an inorganic acid an organic acid or a metal ion; and at least one further fungicidal compound, selected from the group consisting of thiram, fenoxanil, benthivalicarb, metalaxyl, fludioxonil and prochloraz, in a synergistically effective amount and to methods for controlling harmful fungi, comprising applying the fungicidal mixture.

12 Claims, No Drawings

FUNGICIDAL MIXTURES

CROSS REFERENCE TO RELATED APPLICATION(S)

This application is a continuation of U.S. application Ser. No. 10/508,208, filed Sep. 20, 2004, which is a 35 U.S.C. §371 National Phase Entry Application from PCT/EP2003/002845, filed Mar. 19, 2003, and designating the United States. This application also claims the benefit of German Application No. 10212704.2, filed Mar. 21, 2002, the disclosure of which is incorporated herein in its entirety by reference.

BACKGROUND OF THE INVENTION

1. Technical Field

The present invention relates to fungicidal mixtures, comprising
(1) 2-[2-(1-chlorocyclopropyl)-3-(2-chlorophenyl)-2-hydroxypropyl]-2,4-dihydro-[1,2,4]-triazole-3-thione (prothioconazole) of the formula I or a salt or adduct thereof

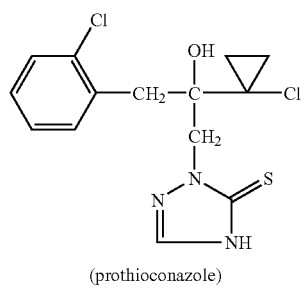

(prothioconazole)

(I)

and at least one further fungicidal compound, selected from the group consisting of
(2) boscalid of formula II

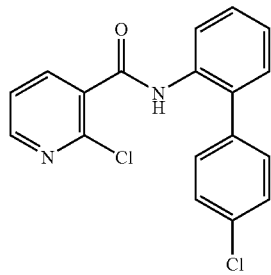

(II)

and
(3) carboxin of formula III

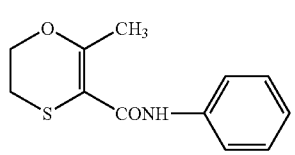

(III)

and
(4) metrafenone of formula IV

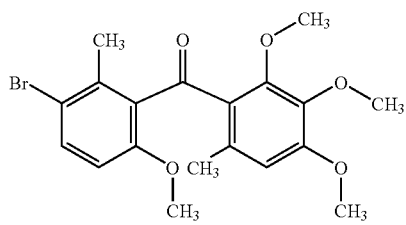

(IV)

and
(5) a compound of formula V

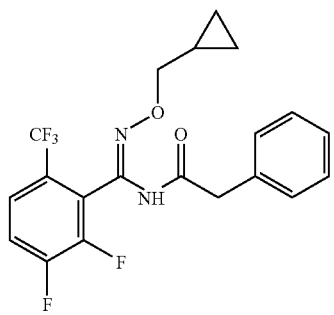

(V)

and
(6) a compound of formula VI

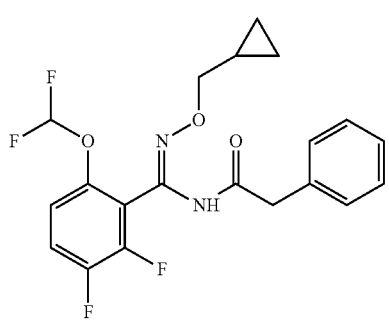

(VI)

and
(7) quinoxyfen of formula VII

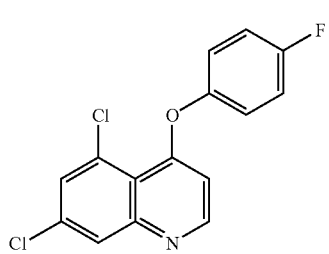

(VII)

and
(8) dithianon of formula VIII
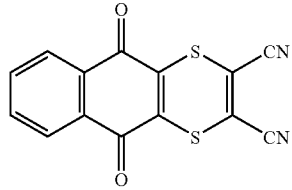
and
(9) thiram of formula IX
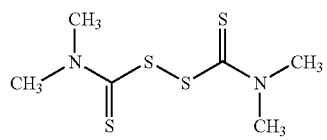
and
(10) mepiquat chloride of formula X
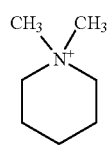
and
(11) cyazofamid of formula XI
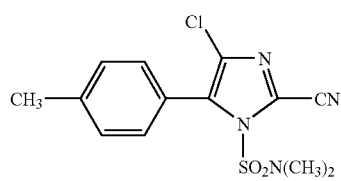
and
(12) fenoxanil of formula XII
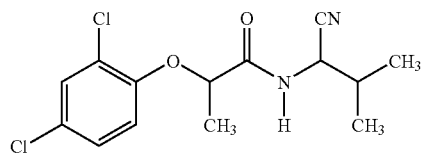
and
(13) a compound of formula XIII
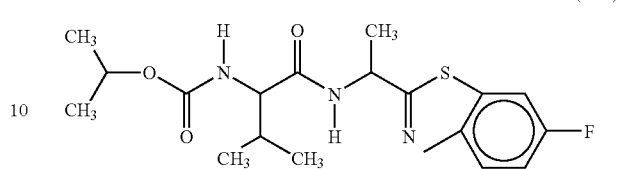
and
(14) thiophanate-methyl of formula XIV
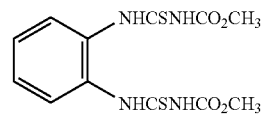
and
(15) carbendazim of formula XV
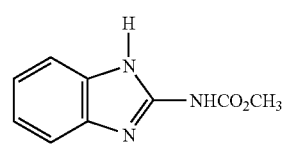
and
(16) metalaxyl of formula XVI
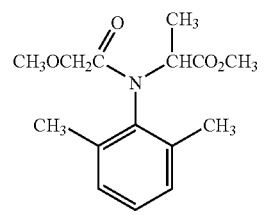
and
(17) fludioxonil of formula XVII
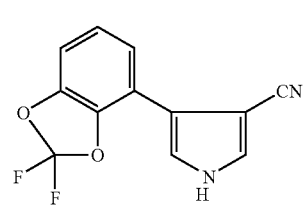

and
(18) thiabendazole of formula XVIII

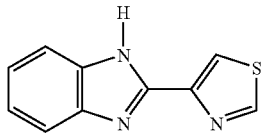 (XVIII)

and
(19) quintozen of formula XIX

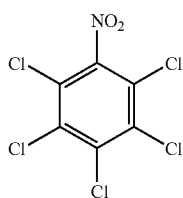 (XIX)

and
(20) prochloraz of formula XX

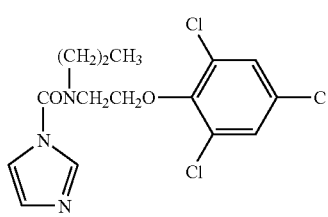 (XX)

and
(21) anthraquinone of formula XXI

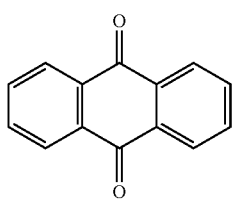 (XXI)

in a synergistically effective amount.

Moreover, the invention relates to a method for controlling harmful fungi using mixtures of the compounds I and at least one of the compounds II to XXI, and to the use of the compounds I and at least one of the compounds II to XXI for preparing such mixtures, and to compositions comprising these mixtures.

2. Description of the Background Art

Prothioconazole of formula I, i.e. 2-[2-(1-chlorocyclopropyl)-3-(2-chlorophenyl)-2-hydroxypropyl]-2,4-dihydro-[1,2,4]triazole-3-thione, is already known from WO 96/16048.

WO 98/47367 discloses a number of active compound combinations of prothioconazole with a large number of other fungicidal compounds.

Boscalid of formula II and its use as crop protection agent are described in EP-B 0 545 099.

Carboxin of formula III is already known and described in U.S. Pat. No. 3,249,499.

Metrafenone of formula IV is likewise known and described in EP-A-727 141, EP-A 897 904, EP-A 899 255 and EP-A-967 196.

The compound of formula V is described in WO 96/19442.

The compound of formula VI is described in EP-A-1017670, EP-A-1017671 and DE 19753519.4.

Quinoxyfen of formula VII is known from EP-A-0 326 330.

Dithianon of formula VIII is described in GB 857 383.

Thiram of formula IX is described in DE-A-06 42 532.

Mepiquat chloride of formula X is known from DE-A-22 07 575.

Cyazofamid of formula XI is described in PCT/EP/02/00237

Fenoxanil of formula XII is described in PCT/EP/01/14785.

The compound of formula XIII is described in WO 99/56551.

Thiophanate-methyl of formula XIV is known from DE-A-1930540.

Carbendazim of formula XV is described in U.S. Pat. No. 3,657,443.

Metalaxyl of formula XVI is described in U.S. Pat. No. 4,151,299.

Fludioxonil of formula XVII is known from EP-A-206 999.

Thiabendazole of formula XVIII is known from U.S. Pat. No. 3,017,415.

Quintozene of formula XIX is described in DE-A-682048.

Prochloraz of formula XX is described in U.S. Pat. No. 3,991,071.

Anthraquinone of formula XXI is described in The Pesticide Manual, 12th Ed. (2000), page 39.

It is an object of the present invention to provide mixtures which have improved activity against harmful fungi combined with a reduced total amount of active compound applied (synergistic mixtures), with a view to reducing the application rates and improving the activity specetrum of the known compounds I to XXI.

We have found that this object is achieved by the mixture, defined at the outset, of prothioconazole with at least one further fungicide. Moreover, we have found that applying the compound I simultaneously, that is jointly or separately, with at least one of the compounds II to XXI or applying the compound I with at least one of the compounds II to XXI in succession provides better control of harmful fungi than is possible with the individual compounds alone.

2-[2-(1-Chlorocyclopropyl)-3-(2-chlorophenyl)-2-hydroxypropyl]-2,4-dihydro-[1,2,4]-triazole-3-thione of the formula I is known from WO 96-16 048. The compound can be present in the "thiono" form of formula I

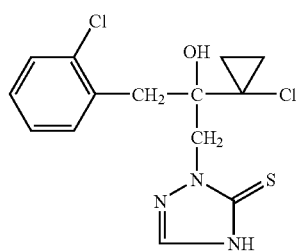 (I)

or in the tautomeric "mercapto" form of formula Ia.

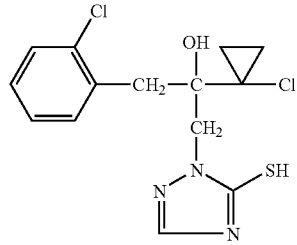
(Ia)

For the sake of simplicity, only the "thiono" form is shown in each case.

Boscalid of formula II

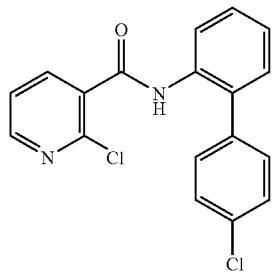
(II)

is known from EP-B-0 545 099.

Carboxin of formula III

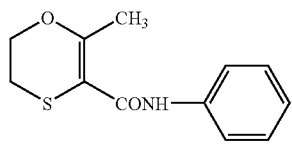
(III)

is known from U.S. Pat. No. 3,249,499.

Metrafenone of formula IV

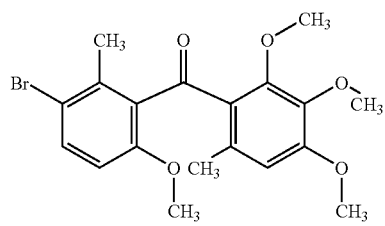
(IV)

is known from EP-A-727 141, EP-A-897 904, EP-A-899 255 and EP-A-96 196.

The compound of formula V

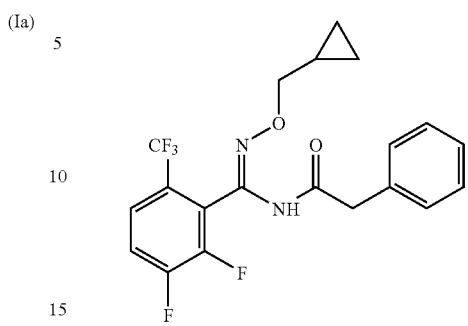
(V)

is known from WO 96/19442.

The compound of formula VI

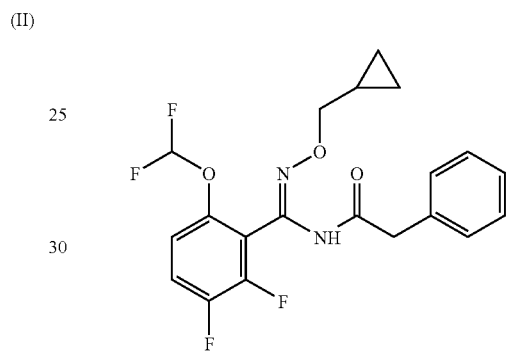
(VI)

is described in EP-A-1017 670, EP-A-1017 671 and DE 197 535 19.4.

Quinoxyfen of formula VII

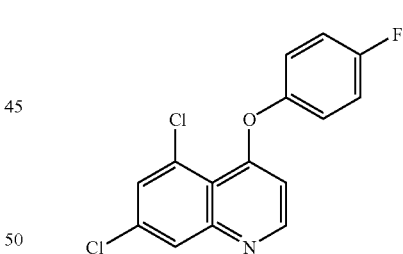
(VII)

is known from EP-A-0 326 330.

Dithianon of formula VIII

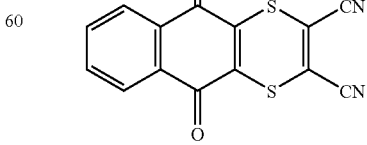
(VIII)

is described in GB 857 383.

Thiram of formula IX

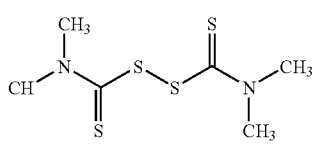
(IX)

is known from DE-A-06 42 532.

Mepiquat chloride of formula X

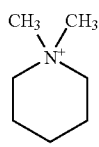
(X)

is described in DE-A-22 07 575.

Cyazofamid of formula XI

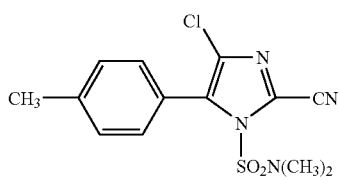
(XI)

is described in PCT/EP/02/00237.

Fenoxanil of formula XII

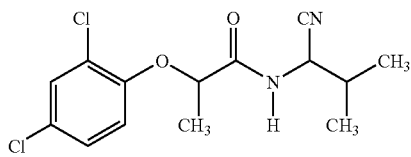
(XII)

is described in PCT/EP/01/14785.

A compound of formula XIII

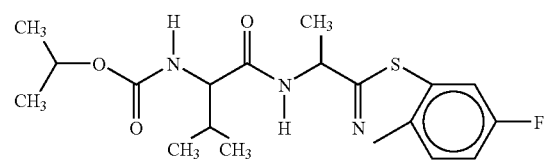
(XIII)

is described in WO 99/56 551.

Thiophanate-methyl of formula XIV

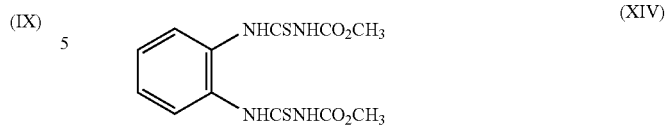
(XIV)

is described in DE-A-1 930 540.

Carbendazim of formula XV

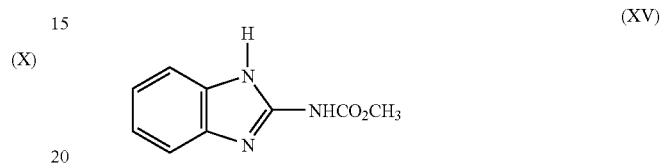
(XV)

is described in U.S. Pat. No. 3,657,443.

Metalaxyl of formula XVI

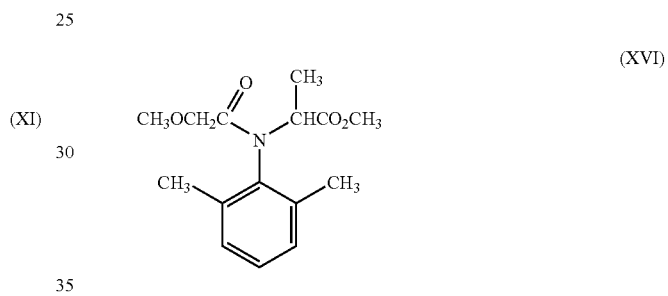
(XVI)

is described in U.S. Pat. No. 4,151,299.

Fludioxonil of formula XVII

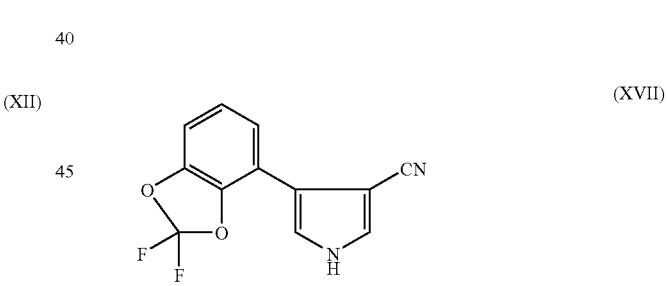
(XVII)

is described in EP-A-206 999.

Thiabendazole of formula XVIII

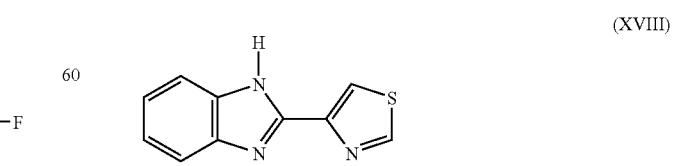
(XVIII)

is described in U.S. Pat. No. 3,017,415.

Quintozene of formula XIX

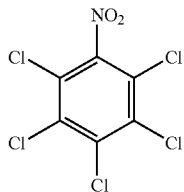

(XIX)

is described in DE-A-682 048.

Prochloraz of formula XX

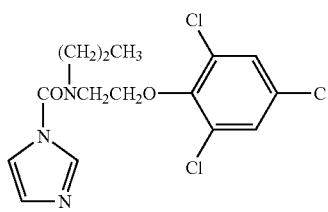

(XX)

is described in U.S. Pat. No. 3,991,071.

Anthraquinone of formula XXI

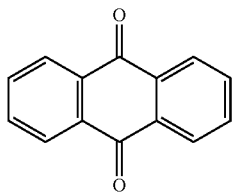

(XXI)

is described in The Pesticide Manual, 12th Ed. (2000), page 39.

SUMMARY OF THE INVENTION

Preference is given to mixtures of prothioconazole with boscalid of the formula II.

Preference is furthermore also given to mixtures of prothioconazole with carboxin of the formula III.

Preference is also given to mixtures of prothioconazole with metrafenone of the formula IV.

Preference is furthermore given to mixtures of prothioconazole with the compound of the formula V.

Preference is furthermore given to mixtures of prothioconazole with the compound of the formula VI.

Preference is furthermore given to mixtures of prothioconazole with quinoxyfen of the formula VII.

Preference is furthermore given to mixtures of prothioconazole with dithianon of the formula VIII.

Preference is furthermore given to mixtures of prothioconazole with thiram of the formula IX.

Preference is furthermore given to mixtures of prothioconazole with mepiquat chloride of the formula X.

Preference is furthermore given to mixtures of prothioconazole with cyazofamid of the formula XI.

Preference is furthermore given to mixtures of prothioconazole with fenoxanil of the formula XII.

Preference is furthermore given to mixtures of prothioconazole with the compound of the formula XIII.

Preference is furthermore given to mixtures of prothioconazole with thiophanate-methyl of the formula XIV.

Preference is furthermore given to mixtures of prothioconazole with carbendazim of the formula XV.

Preference is furthermore given to mixtures of prothioconazole with metalaxyl of the formula XVI.

Preference is furthermore given to mixtures of prothioconazole with fludioxonil of the formula XVII.

Preference is furthermore given to mixtures of prothioconazole with thiabendazole of the formula XVIII.

Preference is furthermore given to mixtures of prothioconazole with quintozene of the formula XIX.

Preference is furthermore given to mixtures of prothioconazole with prochloraz of the formula XX.

Preference is furthermore given to mixtures of prothioconazole with anthraquinone of the formula XXI.

Preference is furthermore given to mixtures of prothioconazole with two further fungicidal compounds of the formulae II to XXI.

DETAILED DESCRIPTION OF THE PREFERRED EMBODIMENTS

Owing to the basic character of its nitrogen atoms, the compound I is capable of forming salts or adducts with inorganic or organic acids or with metal ions.

Examples of inorganic acids are hydrohalic acids, such as hydrogen fluoride, hydrogen chloride, hydrogen bromide and hydrogen iodide, sulfuric acid, phosphoric acid and nitric acid.

Suitable organic acids are, for example, formic acid, carbonic acid and alkanoic acids, such as acetic acid, trifluoroacetic acid, trichloroacetic acid and propionic acid, and also glycolic acid, thiocyanic acid, lactic acid, succinic acid, citric acid, benzoic acid, cinnamic acid, oxalic acid, alkylsulfonic acids (sulfonic acids having straight-chain or branched alkyl radicals of 1 to 20 carbon atoms), arylsulfonic acids or -disulfonic acids (aromatic radicals, such as phenyl and naphthyl, which carry one or two sulfonic acid groups), alkylphosphonic acids (phosphonic acids having straight-chain or branched alkyl radicals of 1 to 20 carbon atoms), arylphosphonic acids or -diphosphonic acids (aromatic radicals, such as phenyl and naphthyl, which carry one or two phosphonic acid radicals), where the alkyl or aryl radicals may carry further substituents, for example p-toluenesulfonic acid, salicylic acid, p-aminosalicylic acid, 2-phenoxybenzoic acid, 2-acetoxybenzoic acid, etc.

Suitable metal ions are in particular the ions of the elements of the second main group, in particular calcium and magnesium, of the third and fourth main group, in particular aluminum, tin and lead, and also of the first to eighth transition group, in particular chromium, manganese, iron, cobalt, nickel, copper, zinc and others. Particular preference is given to the metal ions of the elements of the transition groups of the fourth period. The metals can be present in the various valencies that they can assume.

When preparing the mixtures, it is preferred to employ the pure active compounds I to XXI, to which may be added further active compounds against harmful fungi or against other pests, such as insects, arachnids or nematodes, or else herbicidal or growth-regulating active compounds or fertilizers.

The mixtures of the compound I with at least one of the compounds II to XXI, or the compound I and at least one of the compounds II to XXI applied simultaneously, together or separately, exhibit outstanding activity against a wide range of phytopathogenic fungi, in particular from the classes Ascomycetes, Basidiomycetes, Phycomycetes and Deuteromycetes. Some of them act systemically and can therefore also be employed as foliar- and soil-acting fungicides.

They are especially important for controlling a large number of fungi in a variety of crop plants, such as cotton, vegetable species (for example cucumbers, beans, tomatoes, potatoes and cucurbits), barley, grass, oats, bananas, coffee, corn, fruit species, rice, rye, soya, grapevine, wheat, ornamentals, sugar cane, and a large number of seeds.

They are particularly suitable for controlling the following phytopathogenic fungi: *Blumeria graminis* (powdery mildew) in cereals, *Erysiphe cichoracearum* and *Sphaerotheca fuliginea* in cucurbits, *Podosphaera leucotricha* in apples, *Uncinula necator* in grapevines, *Puccinia* species in cereals, *Rhizoctonia* species in cotton, rice and lawns, *Ustilago* species in cereals and sugar cane, *Venturia inaequalis* (scab) in apples, *Helminthosporium* species in cereals, *Septoria nodorum* in wheat, *Botrytis cinera* (gray mold) in strawberries, vegetables, ornamentals and grapevines, *Cercospora arachidicola* in groundnuts, *Pseudocercosporella herpotrichoides* in wheat and barley, *Pyricularia oryzae* in rice, *Phytophthora infestans* in potatoes and tomatoes, *Plasmopara viticola* in grapevines, *Pseudoperonospora* species in hops and cucumbers, *Alternaria* species in vegetables and fruit, *Mycosphaerella* species in bananas and also *Fusarium* and *Verticillium* species.

The compound I and at least one of the compounds II to XIII can be applied simultaneously, that is together or separately, or in succession, the sequence, in the case of separate application, generally not having any effect on the result of the control measures.

The compounds I and II are usually employed in a weight ratio of from 20:1 to 1:20, in particular from 10:1 to 1:10, preferably from 5:1 to 1:5.

The compounds I and III are usually employed in a weight ratio of from 20:1 to 1:20, in particular from 10:1 to 1:10, preferably from 5:1 to 1:5.

The compounds I and IV are usually employed in a weight ratio of from 20:1 to 1:20, in particular from 10:1 to 1:10, preferably from 5:1 to 1:5.

The compounds I and V are usually employed in a weight ratio of from 20:1 to 1:20, in particular from 10:1 to 1:10, preferably from 5:1 to 1:5.

The compounds I and VI are usually employed in a weight ratio of from 20:1 to 1:20, in particular from 10:1 to 1:10, preferably from 5:1 to 1:5.

The compounds I and VII are usually employed in a weight ratio of from 20:1 to 1:20, in particular from 10:1 to 1:10, preferably from 5:1 to 1:5.

The compounds I and VIII are usually employed in a weight ratio of from 20:1 to 1:20, in particular from 10:1 to 1:10, preferably from 5:1 to 1:5.

The compounds I and IX are usually employed in a weight ratio of from 20:1 to 1:20, in particular from 10:1 to 1:10, preferably from 5:1 to 1:5.

The compounds I and X are usually employed in a weight ratio of from 20:1 to 1:20, in particular from 10:1 to 1:10, preferably from 5:1 to 1:5.

The compounds I and XI are usually employed in a weight ratio of from 20:1 to 1:20, in particular from 10:1 to 1:10, preferably from 5:1 to 1:5.

The compounds I and XII are usually employed in a weight ratio of from 20:1 to 1:20, in particular from 10:1 to 1:10, preferably from 5:1 to 1:5.

The compounds I and XIII are usually employed in a weight ratio of from 20:1 to 1:20, in particular from 10:1 to 1:10, preferably from 5:1 to 1:5.

The compounds I and XIV are usually employed in a weight ratio of from 20:1 to 1:20, in particular from 10:1 to 1:10, preferably from 5:1 to 1:5.

The compounds I and XV are usually employed in a weight ratio of from 20:1 to 1:20, in particular from 10:1 to 1:10, preferably from 5:1 to 1:5.

The compounds I and XVI are usually employed in a weight ratio of from 20:1 to 1:20, in particular from 10:1 to 1:10, preferably from 5:1 to 1:5.

The compounds I and XVII are usually employed in a weight ratio of from 20:1 to 1:20, in particular from 10:1 to 1:10, preferably from 5:1 to 1:5.

The compounds I and XVIII are usually employed in a weight ratio of from 20:1 to 1:20, in particular from 10:1 to 1:10, preferably from 5:1 to 1:5.

The compounds I and XIX are usually employed in a weight ratio of from 20:1 to 1:20, in particular from 10:1 to 1:10, preferably from 5:1 to 1:5.

The compounds I and XX are usually employed in a weight ratio of from 20:1 to 1:20, in particular from 10:1 to 1:10, preferably from 5:1 to 1:5.

The compounds I and XXI are usually employed in a weight ratio of from 20:1 to 1:20, in particular from 10:1 to 1:10, preferably from 5:1 to 1:5.

Depending on the kind of effect desired, the application rates of the mixtures according to the invention are, in particular in agricultural crop areas, from 0.01 to 8 kg/ha, preferably from 0.1 to 5 kg/ha, in particular from 0.1 to 3.0 kg/ha.

The application rates of the compounds I are accordingly from 0.01 to 1 kg/ha, preferably from 0.05 to 0.5 kg/ha, in particular from 0.05 to 0.3 kg/ha.

The application rates of the compounds II are accordingly from 0.01 to 1 kg/ha, preferably from 0.02 to 0.5 kg/ha, in particular from 0.05 to 0.3 kg/ha.

The application rates of the compounds III are accordingly from 0.01 to 1 kg/ha, preferably from 0.02 to 0.5 kg/ha, in particular from 0.05 to 0.3 kg/ha.

The application rates of the compounds IV are accordingly from 0.01 to 1 kg/ha, preferably from 0.02 to 0.5 kg/ha, in particular from 0.05 to 0.3 kg/ha.

The application rates of the compounds V are accordingly from 0.01 to 1 kg/ha, preferably from 0.02 to 0.5 kg/ha, in particular from 0.05 to 0.3 kg/ha.

The application rates of the compounds VI are accordingly from 0.01 to 1 kg/ha, preferably from 0.02 to 0.5 kg/ha, in particular from 0.05 to 0.3 kg/ha.

The application rates of the compounds VII are accordingly from 0.01 to 1 kg/ha, preferably from 0.02 to 0.5 kg/ha, in particular from 0.05 to 0.3 kg/ha.

The application rates of the compounds VIII are accordingly from 0.01 to 1 kg/ha, preferably from 0.02 to 0.5 kg/ha, in particular from 0.05 to 0.3 kg/ha.

The application rates of the compounds IX are accordingly from 0.01 to 1 kg/ha, preferably from 0.02 to 0.5 kg/ha, in particular from 0.05 to 0.3 kg/ha.

The application rates of the compounds X are accordingly from 0.01 to 1 kg/ha, preferably from 0.02 to 0.5 kg/ha, in particular from 0.05 to 0.3 kg/ha.

The application rates of the compounds XI are accordingly from 0.01 to 1 kg/ha, preferably from 0.02 to 0.5 kg/ha, in particular from 0.05 to 0.3 kg/ha.

The application rates of the compounds XII are accordingly from 0.01 to 1 kg/ha, preferably from 0.02 to 0.5 kg/ha, in particular from 0.05 to 0.3 kg/ha.

The application rates of the compounds XIII are accordingly from 0.01 to 1 kg/ha, preferably from 0.02 to 0.5 kg/ha, in particular from 0.05 to 0.3 kg/ha.

The application rates of the compounds XIV are accordingly from 0.01 to 1 kg/ha, preferably from 0.02 to 0.5 kg/ha, in particular from 0.05 to 0.3 kg/ha.

The application rates of the compounds XV are accordingly from 0.01 to 1 kg/ha, preferably from 0.02 to 0.5 kg/ha, in particular from 0.05 to 0.3 kg/ha.

The application rates of the compounds XVI are accordingly from 0.01 to 1 kg/ha, preferably from 0.02 to 0.5 kg/ha, in particular from 0.05 to 0.3 kg/ha.

The application rates of the compounds XVII are accordingly from 0.01 to 1 kg/ha, preferably from 0.02 to 0.5 kg/ha, in particular from 0.05 to 0.3 kg/ha.

The application rates of the compounds XVIII are accordingly from 0.01 to 1 kg/ha, preferably from 0.02 to 0.5 kg/ha, in particular from 0.05 to 0.3 kg/ha.

The application rates of the compounds XIX are accordingly from 0.01 to 1 kg/ha, preferably from 0.02 to 0.5 kg/ha, in particular from 0.05 to 0.3 kg/ha.

The application rates of the compounds XX are accordingly from 0.01 to 1 kg/ha, preferably from 0.02 to 0.5 kg/ha, in particular from 0.05 to 0.3 kg/ha.

The application rates of the compounds XXI are accordingly from 0.01 to 1 kg/ha, preferably from 0.02 to 0.5 kg/ha, in particular from 0.05 to 0.3 kg/ha.

For seed treatment, the application rates used of the mixture are generally from 0.001 to 250 g/kg of seed, preferably from 0.01 to 100 g/kg, in particular from 0.01 to 50 g/kg.

If phytopathogenic harmful fungi are to be controlled, the separate or joint application of the compound I and at least one of the compounds II to XXI or of the mixtures of the compound I with at least one of the compounds II to XXI is effected by spraying or dusting the seeds, the plants or the soils before or after sowing of the plants, or before or after plant emergence.

The fungicidal synergistic mixtures according to the invention or the compound I and at least one of the compounds II to XXI can be formulated, for example, in the form of ready-to-spray solutions, powders and suspensions or in the form of highly concentrated aqueous, oily or other suspensions, dispersions, emulsions, oil dispersions, pastes, dusts, materials for broadcasting or granules, and applied by spraying, atomizing, dusting, broadcasting or watering. The use form depends on the intended purpose; in any case, it should ensure as fine and uniform as possible a distribution of the mixture according to the invention.

The formulations are prepared in a known manner, for example by adding solvents and/or carriers. The formulations are usually admixed with inert additives, such as emulsifiers or dispersants. Fungicidal compositions comprise the fungicidal mixture and a solid or liquid carrier.

Suitable surfactants are the alkali metal salts, alkaline earth metal salts and ammonium salts of aromatic sulfonic acids, for example ligno-, phenol-, naphthalene- and dibutylnaphthalenesulfonic acid, and of fatty acids, alkyl- and alkylarylsulfonates, alkyl, lauryl ether and fatty alcohol sulfates, and also salts of sulfated hexa-, hepta- and octadecanols, or of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ether, ethoxylated isooctyl-, octyl- or nonylphenol, alkylphenyl or tributylphenyl polyglycol ethers, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignosulfite waste liquors or methylcellulose.

Powders, materials for broadcasting and dusts can be prepared by mixing or jointly grinding the compound I and at least one of the compounds II to XXI or the mixture of the compound I with at least one of the compounds II to XXI with a solid carrier.

Granules (for example coated granules, impregnated granules or homogeneous granules) are usually prepared by binding the active compound or active compounds to a solid carrier.

Fillers or solid carriers are, for example, mineral earths, such as silicas, silica gels, silicates, talc, kaolin, limestone, lime, chalk, bole, loess, clay, dolomite, diatomaceous earth, calcium sulfate, magnesium sulfate, magnesium oxide, ground synthetic minerals, and also fertilizers, such as ammonium sulfate, ammonium phosphate, ammonium nitrate, ureas, and products of vegetable origin, such as cereal meal, tree bark meal, wood meal and nutshell meal, cellulose powders or other solid carriers.

The formulations generally comprise from 0.1 to 95% by weight, preferably from 0.5 to 90% by weight, of the compound I and at least one of the compounds II to XXI or of the mixture of the compound I with at least one of the compounds II to XXI. The active compounds are employed in a purity of from 90% to 100%, preferably from 95% to 100% (according to NMR spectrum or HPLC).

The compound I and at least one of the compounds II to XXI, the mixtures, or the corresponding formulations, are applied by treating the harmful fungi, their habitat, or the plants, seeds, soils, areas, materials or spaces to be kept free from them with a fungicidally effective amount of the mixture, or of the compound I and at least one of the compounds II to XXI in the case of separate application.

Application can be effected before or after infection by the harmful fungi.

EXAMPLES

Use Example

The synergistic activity of the mixtures according to the invention was demonstrated by the following experiments:

The active compounds, separately or together, were formulated as a 10% emulsion in a mixture of 85% by weight of cyclohexanone and 5% by weight of emulsifier, and diluted with water to the desired concentration.

Evaluation was carried out by determining the infected leaf areas in percent. These percentages were converted into efficacies. The efficacy (W) was calculated as follows using Abbot's formula:

$$W = \left(1 - \frac{\alpha}{\beta}\right) \cdot 100$$

α corresponds to the fungal infection of the treated plants in % and

β corresponds to the fungal infection of the untreated (control) plants in %.

An efficacy of 0 means that the infection level of the treated plants corresponds to that of the untreated control plants; an efficacy of 100 means that the treated plants were not infected.

The expected efficacies of the mixtures of the active compounds were determined using Colby's formula [R. S. Colby, Weeds 15, 20-22 (1967)] and compared with the observed efficacies.

Colby formula: $E = x + y - xy/100$

E expected efficacy, expressed in % of the untreated control, when using the mixture of the active compounds A and B at the concentrations a and b x efficacy, expressed in % of the untreated control, when using active compound A at a concentration of a y efficacy, expressed in % of the untreated control, when using active compound B at a concentration of b.

Use example 1: Activity against mildew of wheat caused by *Erysiphe* [syn. *Blumeria*] *graminis* form a specialis. *tritici*

Leaves of wheat seedlings of the cultivar "Kanzler", grown in pots, were sprayed to runoff point with an aqueous preparation of active compound which had been prepared from a stock solution comprising 10% of active compound, 85% of cyclohexanone and 5% of emulsifier, and 24 hours after the spray coating had dried on, the leaves were dusted with spores of mildew of wheat (*Erysiphe* [syn. *Blumeria*] *graminis* form a specialis. *tritici*). The test plants were then placed in a greenhouse at 20-24° C. and 60-90% relative atmospheric humidity. After 7 days, the extent of the mildew development was determined visually in % infection of the entire leaf area.

The visually determined values for the percentage of diseased leaf areas were converted into efficacies in % of the untreated control. An efficacy of 0 means the same disease level as in the untreated control, an efficacy of 100 means a disease level of 0%. The expected efficacies for the combinations of active compounds were determined using Colby's formula, mentioned above, and compared with the observed efficacies.

TABLE 1

| Active compound | Concentration of active compound in the spray liquor in ppm | Efficacy in % of the untreated control |
|---|---|---|
| Control (untreated) | (90% infection) | 0 |
| Compound I = prothioconazole | 4 | 42 |
|  | 1 | 0 |
|  | 0.25 | 0 |
| Compound II = boscalid | 4 | 0 |
|  | 1 | 0 |
|  | 0.25 | 0 |
|  | 0.06 | 0 |
| Compound IV = metrafenone | 0.06 | 53 |
|  | 0.015 | 30 |
| Compound VI | 0.25 | 53 |
|  | 0.06 | 0 |
| Compound VIII = dithianon | 4 | 0 |
|  | 1 | 0 |
|  | 0.25 |  |
| Compound XI = cyazofamid | 1 | 22 |
|  | 0.25 | 22 |
|  | 0.06 | 0 |

TABLE 2

| Combinations according to the invention | Observed efficacy | Calculated efficacy*) |
|---|---|---|
| Compound I = prothioconazole + Compound II = boscalid 0.25 + 4 ppm mixture 1:16 | 19 | 0 |
| Compound I = prothioconazole + Compound II = boscalid 1 + 4 ppm mixture 1:4 | 92 | 0 |
| Compound I = prothioconazole + Compound II = boscalid 0.25 + 1 ppm mixture 1:4 | 53 | 0 |
| Compound I = prothioconazole + Compound II = boscalid 1 + 0.25 ppm mixture 4:1 | 30 | 0 |
| Compound I = protioconazole + Compound II = boscalid 1 + -.06 ppm mixture 16:1 | 19 | 0 |
| Compound I = prothioconazole + Compound IV metrafenone 0.25 + 0.06 ppm mixture 4:1 | 65 | 53 |
| Compound I = prothioconazole + Compound IV metrafenone 1 + 0.06 ppm mixture 16:1 | 65 | 53 |
| Compound I = prothioconazole + Compound IV metrafenone 0.25 + 0.015 ppm mixture 16:1 | 42 | 30 |
| Compound I = prothioconazole + Compound VI 1 + 0.25 ppm mixture 1:16 | 65 | 53 |
| Compound I = prothioconazole + Compound VI 0.25 + 0.06 ppm mixture 4:1 | 18 | 0 |
| Compound I = prothioconazole + Compound VI 4 + 0.25 ppm mixture 16:1 | 88 | 77 |
| Compound I = prothioconazole + Compound VII = dithianon 0.25 + 4 ppm mixture 1:16 | 33 | 0 |
| Compound I = prothioconazole + Compound VII = dithianon 1 + 4 ppm mixture 1:4 | 33 | 0 |
| Compound I = prothioconazole + Compound VII = dithianon 0.25 + 0.25 ppm mixture 1:1 | 97 | 0 |
| Compound I = prothioconazole + Compound VII = dithianon 1 + 0.25 ppm mixture 4:1 | 22 | 0 |
| Compound I = prothioconazole + Compound XI = cyazofamid 0.06 + 1 ppm mixture 16:1 | 56 | 22 |
| Compound I = prothioconazole + Compound XI = cyazofamid 1 + 0.25 ppm mixture 4:1 | 56 | 22 |
| Compound I = prothioconazole + Compound XI = cyazofamid 1 + 0.25 ppm mixture 4:1 | 33 | 22 |
| Compound I = prothioconazole + Compound XI = cyazofamid 1 + 0.06 ppm mixture 16:1 | 22 | 0 |

*)Efficacy calculated using Colby's formula

The test results show that in all mixing ratios the observed efficacy is higher than the efficacy calculated beforehand using Colby's formula (from Synerg 176. SLX)

Use example 2: Protective activity against mildew of cucumber caused by *Sphaerotheca fuliginea*

Leaves of cucumber seedlings of the cultivar "chinese snake", grown in pots, were, at the cotyledon stage, sprayed to runoff point with an aqueous preparation of active compound which had been prepared from a stock solution comprising 10% of active compound, 85% of cyclohexanone and 5% of emulsifier. 20 hours after the spray coating had dried on, the plants were inoculated with an aqueous spore suspension of mildew of cucumber (*Sphaerotheca fuliginea*). The plants were then cultivated in a greenhouse at 20-24° C. and 60-80% relative atmospheric humidity for 7 days. The extent of the mildew development was then determined visually in % infection of the cotyledon area. The visually determined values for the percentage of diseased leaf areas were converted into efficacies in % of the untreated control. An efficacy of 0 means the same disease level as in the untreated control, an efficacy of 100 means a disease level of 0%. The expected efficacies for the combinations of active compounds were determined using Colby's formula, mentioned above, and compared with the observed efficacies.

TABLE 3

| Active compound | Concentration of active compound in the spray liquor in ppm | Efficacy in % of the untreated control |
|---|---|---|
| Control (untreated) | (90% infection) | 0 |
| Compound I = prothioconazole | 1 | 78 |
| | 0.25 | 56 |
| Compound II = boscalid | 4 | 78 |
| | 0.25 | 0 |
| | 0.06 | 0 |
| Compound IV = metrafenone | 0.06 | 0 |
| | 0.015 | 0 |
| Compound VI | 0.06 | 33 |
| | 0.015 | 0 |

TABLE 4

| Combinations according to the invention | Observed efficacy | Calculated efficacy*) |
|---|---|---|
| Compound I = prothioconazole + Compound II = boscalid 0.25 + 4 ppm mixture 1:16 | 99 | 90 |
| Compound I = prothioconazole + Compound II = boscalid 1 + 0.25 ppm mixture 4:1 | 89 | 78 |
| Compound I = prothioconazole + Compound II = boscalid 0.25 + 0.06 ppm mixture 4:1 | 78 | 56 |
| Compound I = prothioconazole + Compound II = boscalid 1 + 0.06 ppm mixture 16:1 | 94 | 78 |
| Compound I = prothioconazole + Compound IV = metrafenone 0.25 + 0.06 ppm mixture 4:1 | 78 | 56 |
| Compound I = prothioconazole + Compound IV = metrafenone 1 + 0.06 ppm mixture 16:1 | 94 | 78 |
| Compound I = prothioconazole + Compound IV = metrafenone 0.25 + 0.015 ppm mixture 16:1 | 78 | 56 |
| Compound I = prothioconazole + Compound VI 0.25 + 0.06 ppm mixture 4:1 | 89 | 70 |
| Compound I = prothioconazole + Compound VI 0.25 + 0.015 ppm mixture 16:1 | 72 | 56 |

*)Efficacy calculated using Colby's formula

The test results show that in all mixing ratios the observed efficacy is higher than the efficacy calculated beforehand using Colby's formula (from Synerg 176. SLX)

The invention claimed is:

1. A fungicidal mixture, comprising
(a) 2-[2-(1-chlorocyclopropyl)-3-(2-chlorophenyl)-2-hydroxypropyl]-2,4-dihydro-[1,2,4]-triazole-3-thione (prothioconazole) of the formula I

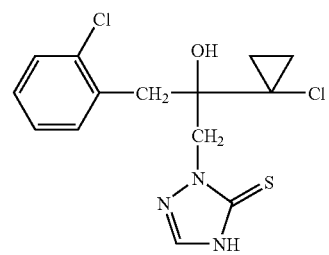

(I)

or a salt or adduct thereof with an inorganic acid an organic acid or a metal ion; and
(b) at least one further fungicidal compound, selected from the group consisting of
(1) thiram of the formula IX

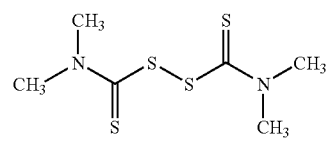

(IX)

(2) fenoxanil of the formula XII

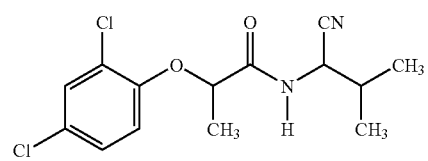

(XII)

(3) benthivalicarb of the formula XIII

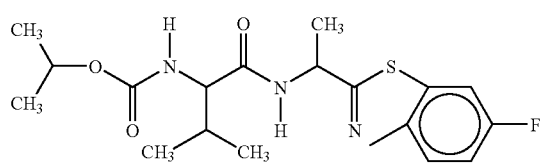

(XIII)

(4) metalaxyl of the formula XVI

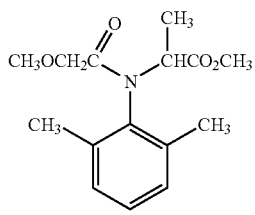

(5) fludioxonil of the formula XVII

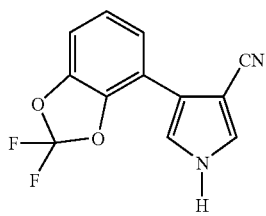

and
(6) prochloraz of the formula XX

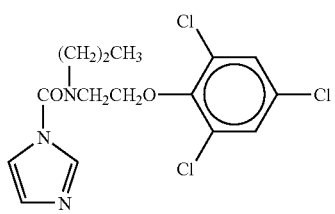

in a synergistically effective amount.

2. The fungicidal mixture of claim 1 comprising prothioconazole or a salt or adduct thereof with an inorganic acid an organic acid or a metal ion and thiram.

3. The fungicidal mixture of claim 1 comprising prothioconazole or a salt or adduct thereof with an inorganic acid an organic acid or a metal ion and fenoxanil.

4. The fungicidal mixture of claim 1 comprising prothioconazole or a salt or adduct thereof with an inorganic acid an organic acid or a metal ion and benthivalicarb.

5. The fungicidal mixture of claim 1 comprising prothioconazole or a salt or adduct thereof with an inorganic acid an organic acid or a metal ion and metalaxyl.

6. The fungicidal mixture of claim 1 comprising prothioconazole or a salt or adduct thereof with an inorganic acid an organic acid or a metal ion and fludioxonil.

7. The fungicidal mixture of claim 1 comprising prothioconazole or a salt or adduct thereof with an inorganic acid an organic acid or a metal ion and prochloraz.

8. The fungicidal mixture of claim 1 further comprising a solid or liquid carrier.

9. A method for controlling harmful fungi, comprising applying the fungicidal mixture of claim 1 to the harmful fungi, their habitat or plants, seeds, soils, areas, materials or spaces to be kept free from the fungi.

10. A method for controlling harmful fungi of claim 9, comprising applying prothioconazole and said further fungicidal compound simultaneously to the harmful fungi, their habitat or plants, seeds, soils, areas, materials or spaces to be kept free from the fungi.

11. A method for controlling harmful fungi of claim 9, comprising applying prothioconazole and said further fungicidal compound separately to the harmful fungi, their habitat or plants, seeds, soils, areas, materials or spaces to be kept free from the fungi.

12. A method of claim 9 comprising applying said fungicidal mixture in an amount of from 0.01 to 8 kg/ha.

\* \* \* \* \*